United States Patent [19]

Milberger et al.

[11] 4,351,773

[45] Sep. 28, 1982

[54] PREPARATION OF MALEIC ANHYDRIDE FROM BUTANE USING FLUIDIZED VANADIUM-PHOSPHOROUS-OXIDE CONTAINING CATALYSTS

[75] Inventors: Ernest C. Milberger, Solon; Michael F. Lemanski, Cleveland, both of Ohio; Gregory G. Spitnale, Kalamazoo, Mich.

[73] Assignee: The Standard Oil Company, Cleveland, Ohio

[21] Appl. No.: 221,670

[22] Filed: Dec. 31, 1980

[51] Int. Cl.$^3$ .......................................... C07D 307/60
[52] U.S. Cl. .................................... 549/259; 252/437
[58] Field of Search ...................................... 260/346.75

[56] References Cited

U.S. PATENT DOCUMENTS

| | | | |
|---|---|---|---|
| 3,888,886 | 6/1975 | Young et al. | 260/346.75 |
| 3,905,914 | 9/1975 | Jurewicz et al. | 260/346.75 |
| 3,931,046 | 1/1976 | Weinstein et al. | 260/346.75 |
| 3,932,305 | 1/1976 | Jurewicz et al. | 260/346.75 |
| 3,975,300 | 8/1976 | Burress | 252/435 |
| 4,002,650 | 1/1977 | Bremer et al. | 260/346.75 |
| 4,003,943 | 8/1977 | Schneider | 252/437 |

FOREIGN PATENT DOCUMENTS 2022271 7/1970 France.

*Primary Examiner*—Henry R. Jiles
*Assistant Examiner*—Bernard Dentz
*Attorney, Agent, or Firm*—Joseph G. Curatolo; Herbert D. Knudsen; Larry W. Evans

[57] ABSTRACT

A process is provided for the preparation of fluid bed oxidation catalysts containing the mixed oxides of vanadium and phosphorus, comprising the steps of preparing the catalyst precursor, comminuting the precursor, introducing the precursor into water to form an aqueous slurry and spray drying the slurry. The resulting microspheroidal particles are excellent fluid bed catalysts for the preparation of maleic anhydride from 4-carbon atom hydrocarbons.

12 Claims, No Drawings

PREPARATION OF MALEIC ANHYDRIDE FROM BUTANE USING FLUIDIZED VANADIUM-PHOSPHOROUS-OXIDE CONTAINING CATALYSTS

BACKGROUND OF THE INVENTION

This invention relates to a method for preparing fluid bed catalysts useful in the production of dicarboxylic acid anhydrides by the oxidation of hydrocarbons. More particularly it is directed to the preparation of fluid bed catalysts suitable for producing maleic anhydride from 4-carbon atom hydrocarbons, such as n-butane, n-butenes, 1,3 butadiene or a mixture thereof.

The advantages of fluid bed hydrocarbon oxidation processes compared to fixed bed hydrocarbon oxidation processes are well known in the art, including the improvement of temperature control and heat transfer for oxidation reactions. Catalysts which are suitable for fixed bed processes are not necessarily suitable for fluid bed processes. Despite the incentive to utilize fluid bed technology in the production of maleic anhydride from 4-carbon atom hydrocarbons, there currently is no commercial fluid bed plant of this type in operation, all such commercial plants being fixed bed operations.

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride. Conventional methods of preparing these catalysts involve reducing a pentavalent vanadium compound, and combining the same with a phosphorus compound, and if desired, promoter element compounds under conditions which will provide vanadium in a valence state below +5 to form catalyst precursors capable of being converted to an oxide. The catalyst oxide precursor is then recovered and calcined, before or after the fixed bed catalyst particles are formed, to provide active catalytic material.

U.S. Pat. Nos. 3,888,886; 3,905,914; 3,931,046; 3,932,305 and 3,975,300 disclose the testing of promoted vanadium phosphorus oxide catalysts for maleic anhydride production from butane in one inch diameter fluid bed reactors. In most instances, the catalysts were prepared by forming the catalyst precursor in aqueous media (in U.S. Pat. No. 3,975,300 the precursor was formed in a paste of a vanadium compound, a phosphorus compound and an organic reducing agent), drying and thereafter grinding and sieving the precursor to a powder of about 74 to 250 microns size. This manner of preparation, however, does not obtain the uniform, microspheroidal catalyst particles preferred for successful fluid bed operation.

Commercial fluid bed catalysts are preferably microspheroidal particles within the range of about 20 to about 300 microns in average diameter, preferably having about 80% of the particles within the range of about 30 to about 80 microns in diameter. Most preferably, about 25 to about 40% of the particles have an average diameter of less than 45 microns.

It is therefore an object of the invention to provide a process of preparing fluid bed vanadium and phosphorus mixed oxide containing oxidation catalysts.

It is a further object of the invention to provide a process for producing maleic anhydride from 4-carbon atom hydrocarbons utilizing fluid bed vanadium phosphorus mixed oxide catalysts.

SUMMARY OF THE INVENTION

We have found that excellent uniform, microspheroidal vanadium phosphorus mixed oxide containing catalysts, useful in the production of maleic anhydride from 4-carbon atom hydrocarbons in fluid bed operations, can be obtained by spray drying an aqueous slurry of the catalyst precursor. Although this method of preparation may be utilized in forming fluid bed vanadium phosphorus mixed oxide catalysts prepared in aqueous media, it is unexpectedly efficacious when utilized in forming such catalysts in which the precursor was prepared in organic liquid solution or slurry.

It had previously been found that the preparation of vanadium phosphorus mixed oxide precursors in organic liquid media, solutions or slurries, particularly if maintained as essentially anhydrous, resulted in catalysts of high surface area and enhanced activity for the production of maleic anhydride from 4-carbon atom hydrocarbons. The presence of an excess of water in the final stages of preparation diminished both the surface area and activity of the catalyst. The formation of fluid bed catalysts by spray drying an organic liquid slurry of the catalyst precursor, because of flammability of the organic media, is not preferred.

We have found that once the vanadium-phosphorus mixed oxide precursor has been formed, it may be introduced into water to form an aqueous slurry which may then be spray dried to form microspheroidal fluid bed catalysts, without adversely affecting the surface area or activity of the catalyst.

In general, the process of the invention includes the steps of
(a) preparing a vanadium-phosphorus mixed oxide containing catalyst precursor;
(b) comminuting the catalyst precursor,
(c) introducing the catalyst precursor into water prior or subsequent to said comminuting step to form an aqueous slurry, and
(d) spray drying said slurry to form microspheroidal catalyst particles.

DETAILED DESCRIPTION OF THE INVENTION

Catalyst precursors of vanadium phosphorus mixed oxide catalysts for hydrocarbon oxidation may be prepared according to methods known in the art.

U.S. Pat. No. 4,002,650 discloses the preparation of vanadium and phosphorus mixed oxide containing catalysts by reacting vanadium and phosphorus compounds in an aqueous solution, with HCl being utilized as a solvating and reducing agent for vanadium. Similar preparational techniques are described in European Patent Appln. No. 3,431 in which the additional step of comminuting the vanadium-phosphorus precursor to a particle size of 500 to 700 microns (0.5 to 0.7 mm) is disclosed.

U.S. Pat. No. 4,043,943 discloses the preparation of the catalyst precursor in a liquid organic medium, preferably anhydrous, wherein the vanadium compound is reduced and solvated by gaseous HCl followed by reaction with the phosphorus compound.

The preparation of oxidation catalysts containing the mixed oxides of vanadium and phosphorus is disclosed in copending U.S. Ser. No. 106,786, assigned to our common assignee, and now U.S. Pat. No. 4,244,879 wherein a vanadium compound is at least partially solubilized in an organic liquid medium capable of reducing at least a portion of the vanadium to a +4 valence state, and unsolubilized vanadium having a particle size larger than about 0.1 mm diameter is removed from the medium before addition of a phosphorus-containing compound. The preparation of such catalysts is disclosed in co-pending U.S. Ser. No. 146,971, assigned to our common assignee, and now U.S. Pat. No. 4,333,853 wherein partial reduction of a pentavalent vanadium compound is effected in the presence of a phosphorus compound in an organic liquid medium capable of reducing the vanadium.

The catalyst precursor may be recovered from the liquid reaction medium in which it was prepared (preferably an essentially anhydrous maintained organic liquid medium) by conventional methods, such as evaporation, filtration, centrifugation, decanting, and the like. Preferably, the precursor is dried by heating. Alternatively, the recovered precursor, which is still partially wet with the organic liquid, may be treated with a low boiling solvent such as petroleum ether. In another embodiment, excess preparational reaction media may be substantially removed by vacuum filtration. In yet another embodiment, excess water can be introduced into the precursor containing organic liquid reaction medium, allowing an organic layer to separate from the aqueous layer.

After recovery, the catalyst precursor is introduced into water to form an aqueous slurry. The catalyst precursor generally has a particle size of greater than one micron average diameter before it is comminuted. It is preferred, however, that a substantial portion of the catalyst precursor be reduced in particle size to less than one micron, and preferably less than one half micron average diameter. This step of comminuting may be accomplished before the precursor is recovered from its reaction media, or after recovery. Comminution after recovery can be effected either prior or subsequent to introduction into water. For example, dried catalyst precursor particles may be dry milled, such as by ball milling, or the catalyst precursor containing aqueous slurry may be ball milled.

The catalyst precursor preferably should be uncalcined when introduced into water. Substantial contacting of the calcined vanadium phosphorus mixed oxide catalyst with water (at less than 100° C.) reduces the activity of the catalyst, particularly if calcined in air.

The solids content of the catalyst precursor containing aqueous slurry should be adjusted to about 25 to about 60 weight percent. The catalyst precursor-containing aqueous slurry is then spray dried to form uniform, microspheroidal particles having a particle size range of between about 20 to about 300 microns, generally between 20 to about 240 microns. Spray drying may be accomplished by methods known in the art.

The catalyst precursor may contain promoter elements, including but not limited to U, Co, Mo, Fe, Zn, Hf, Zr or mixtures thereof. These may be incorporated into the catalyst precursor in any of the methods known in the art, such as inclusion via the liquid reaction medium prior to or after reduction of the vanadium.

Inert diluents or supports may be added to the fluid bed catalyst, such as by addition of the diluent or support to the aqueous slurry prior to spray drying.

Catalysts suitable for the production of maleic anhydride from 4-carbon atom hydrocarbons generally have a phosphorus to vanadium ratio of about 3:1 to about 0.5:1. Preferred is a P/V ratio of about 1.2:1. These catalysts preferably exhibit an average valence for vanadium within the range of +3.5 to +4.6.

The catalyst may be calcined in air or an oxygen-containing gas at a temperature of 250° C. to 600° C. for a period of up to 5 hours or more. One method of calcination of the catalyst is accomplished by heating the catalyst in a mixture of steam and air or air alone over the catalyst at a temperature of about 300° C. to 500° C. for a period of about 1 to 5 hours. The catalyst may also be calcined in the presence of hydrocarbon, an inert gas, or both. The fluid bed catalyst prepared by the process of the present invention may be utilized in oxidation type fluid bed reactors known in the art.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to the hydrocarbon may range from about 3 to about 30 moles of oxygen per mole of hydrocarbon. Preferred oxygen/hydrocarbon ratios are about 4 to about 20 moles of oxygen per mole of hydrocarbon.

The reaction temperature may vary widely and is dependent upon the particular hydrocarbon and catalyst employed. Normally, temperatures of about 250° C. to about 600° C. are employed with temperatures of 325° C. to 500° C. being preferred. The contact time may be as low as a fraction of a second or as high as 50 seconds. The reaction may be conducted at atmospheric, superatmospheric or subatmospheric pressure. Operation at superatmospheric pressure is preferred, from greater than one atmosphere to about three atmospheres.

SPECIFIC EMBODIMENTS OF THE INVENTION

The fluid bed catalyst described in Examples 1–8, below, were used to produce maleic anhydride from n-butane in an 80 cc fluid bed reactor consisting of about a 35.5 cm length of stainless steel tubing having an outer diameter of about 3.8 cm, having a stainless steel frit at the bottom of the tube to act as a gas (air) distributor and an axial 1.3 cc outer diameter gas (hydrocarbon) sparger/thermowell. The assembly contained an aluminum block pre-heater for the gases, and heating of the reactor unit was accomplished by placement in a temperature controlled molten salt bath.

The fluid bed catalysts described in Examples 9–47, below, were used to produce maleic anhydride from n-butane in a 440 cc fluid bed reactor consisting of about a 61 cm length of stainless steel tubing having an outer diameter of about 3.8 cm, having a stainless steel sparger at the bottom of the tube to act as a gas (air) distributor, with an axial 0.64 cm outer diameter thermowell and a separate hydrocarbon inlet at the bottom of the tube. The reactor was fitted with internal gas redistributing baffles. Gas preheating and reactor temperature control was accomplished by placement of the reactor unit in a thermostated fluidized sand bath.

Flasks for receiving the product maleic anhydride were air cooled, and tail gases were routed to a Carle Analytical Gas Chromatograph III for analysis. Reaction conditions and results of the tests run are described in Tables I through III. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield}}{\text{Total Conversion}} \times 100$$

The throughput of hydrocarbon feed in the production of maleic anhydride, or the working rate imposed upon the catalyst is designated in the tables as WWH, or weight of feed/weight of catalyst/hour.

EXAMPLES 1–7

Fluid bed catalyst having the formula $V_{1.0}P_{1.2}Co_{0.2}O_x$, (where x=number of oxygens needed to satisfy the valence requirements of the other elements) was prepared by the following procedure. 1008 g vanadium pentoxide and 528.2 g cobaltous chloride dihydrate were added to 5.5 liters isobutanol with stirring to form a slurry. Anhydrous hydrogen chloride gas was bubbled through the liquid medium which was maintained by cooling at a temperature of about $20°\pm 5°$ C. After dissolution and reduction of the vanadium (about 4 hours, at which time the temperature of the now-homogenous red-brown solution began to drop, 1303 g 100% ortho-phosphoric acid in 2 liters isobutanol was added to the liquid medium. The liquid medium was then refluxed for about 2 hours, acquiring a blue-green color. The solution was dried via evaporation at a temperature of 150° C. The dried material was ground to yield a powdered catalyst precursor.

1500 g of the catalyst precursor powder was mixed with 3 liters water and the resulting slurry was milled for about 12 hours. The comminuted catalyst precursor containing slurry was spray dried and calcined in air at 400° C. for 16 hours. The resulting catalyst particles were dark green in color and were microspheroidal in form. Results of the fluid bed (80 cc) production of maleic anhydride from n-butane using the catalyst of Examples 1–7 are listed in Table I.

EXAMPLE 8

Fluid bed catalyst having the formula $V_{1.0}P_{1.2}U_{0.2}O_x$ was prepared according to the procedure set forth in Examples 1–7 above, except that 935.5 g uranyl acetate dihydrate was substituted for the cobalt compound. Results of the fluid bed (80 cc) production of maleic anhydride from n-butane using the catalyst of Example 8 are listed in Table I.

EXAMPLES 9–20

Fluid bed catalyst having the formula $V_{1.0}P_{1.2}Co_{0.2}O_x$ was prepared according to the procedure set forth in Examples 1–7 above. Results of the fluid bed (440 cc) production of maleic anhydride from n-butane using the catalyst of Examples 9–20 are listed in Table II.

EXAMPLES 21–27

Fluid bed catalyst having the formula $V_{1.0}P_{1.2}O_x$ was prepared according to the following procedure. Catalyst precursor was prepared by introducing 7.276 kg $V_2O_5$, and about 10.5 kg mixed phosphoric acid (including about 1.2 kg $H_2O$) into 120 liters isobutanol with stirring, and refluxing the resulting slurry for about 6 hours. The mixed phosphoric acid source contained about 87% orthophosphoric acid, 11.5% pyrophosphoric acid and about 1.5% triphosphoric acid based upon total weight of phosphoric acid. The slurry was cooled, the catalyst precursor recovered by filtration and dried for about 3 hours at 150° C.

The dried catalyst precursor was ball milled for about 5.5 hours, and 3000 g comminuted catalyst precursor was thereafter introduced into 3667 g water with stirring. The resulting slurry was spray dried to yield uniform, microspheroidal catalyst particles. Results of the fluid bed (440 cc) production of maleic anhydride from n-butane using the catalyst of Examples 21–27 are listed in Table III.

EXAMPLES 28–37

Fluid bed catalyst having the formula 80 wt.% $V_{1.0}P_{1.2}O_x$/20 wt. % $SiO_2$ was prepared according to the following procedure. About 2.5 kg dry, comminuted catalyst precursor, prepared as in Examples 21–27 was introduced into about 2.6 kg water, containing about 1.8 kg Nalco 1034A silica sol (trade designation of Nalco Chemical Co.), with stirring. The resulting slurry was spray dried to yield uniform, microspheroidal catalyst particles. Results of the fluid bed (440 cc) production of maleic anhydride from n-butane using the catalyst of Examples 28–37 are listed in Table III.

EXAMPLES 38–47

Fluid bed catalyst having the formula 70 wt.% $V_{1.0}P_{1.2}O_x$/30 wt. % $SiO_2$ was prepared according to the following procedure. Catalyst precursor was prepared by introducing 7.276 kg $V_2O_5$ and 9.39 kg orthophosphoric acid (100%) in 120 liters of isobutanol with stirring, and refluxing the resulting slurry for about 16 hours. The slurry was cooled, the catalyst precursor recovered by filtration and dried for about 2 hours at 150° C.

The dried catalyst precursor was ball milled for about 24 hours, and about 844 g comminuted catalyst precursor was introduced into about 2000 g water containing about 1063 g Nalco 1034A silica sol, with stirring. The resulting slurry was spray dried to yield uniform, microspheroidal catalyst particles. Results of the fluid bed (440 cc) production of maleic anhydride from n-butane using the catalyst of Examples 38–47 are listed in Table III.

As can be seen from the results listed in Tables I through III, fluid bed catalysts containing the mixed oxides of vanadium and phosphorus may be prepared according to the present invention, such catalysts being useful in the production of maleic anhydride from 4-carbon atom hydrocarbons. The fluid bed catalysts thus prepared are uniform, microspheroidal, and are suitable for use as commercial fluid bed catalysts, a substantial portion of the microspheroidal particles of such catalysts having particle sizes within the range of about 20 microns to about 100 microns. The particle size requirement for fluid bed catalysts, set forth above, are met by these catalysts. Catalyst precursors which have been prepared in organic media, unexpectedly retain their high activity for the production of maleic anhydride, when further treated according to the process of the present invention.

Thus it should be apparent to those skilled in the art that the subject invention accomplishes the objects set forth above. It is to be understood that the subject invention is not to be limited by the examples set forth herein. These have been provided merely to demonstrate operability, and the selection of methods of preparation of the vanadium and phosphorus mixed oxide containing catalyst precursors, promoter elements if any, inert diluents or supports, if any, methods of comminution, hydrocarbon feedstocks and reaction conditions can be determined from the total specification disclosure provided without departing from the spirit of the invention herein disclosed and described, the scope of the invention including modifications and variations that fall within the scope of the attached claims.

TABLE I

FLUID BED (80 CC) PRODUCTION OF MALEIC ANHYDRIDE FROM n-BUTANE

| Example No. | Temperature °C. Bath | Temperature °C. Bed | Ratio Air/ Hydrocarbon | Contact Time (Sec.) | WWH | % Conversion | Maleic Anhydride % Yield | Maleic Anhydride % Selectivity | Time On Stream (Hrs.) |
|---|---|---|---|---|---|---|---|---|---|
| $V_{1.0}P_{1.2}Co_{0.2}O_x$ Catalyst | | | | | | | | | |
| 1 | 389 | 390 | 66.7 | 6.6 | 0.015 | 92.0 | 58.6 | 63.7 | 66 |
| 2 | 389 | 390 | 64.0 | 6.6 | 0.016 | 76.6 | 48.8 | 63.7 | 165 |
| 3 | 375 | 373 | 72.3 | 6.2 | 0.011 | 93.9 | 64.1 | 68.3 | 72 |
| 4 | 375 | 373 | 61.8 | 6.0 | 0.014 | 86.1 | 58.5 | 68.0 | 139 |
| 5 | 376 | 375 | 65.7 | 6.0 | 0.013 | 89.0 | 58.8 | 66.5 | 166 |
| 6 | 377 | 375 | 67.0 | 6.1 | 0.012 | 79.6 | 50.5 | 63.6 | 265 |
| 7 | 375 | 375 | 65.8 | 6.1 | 0.013 | 81.7 | 52.6 | 64.7 | 310 |
| $V_{1.0}P_{1.2}U_{0.2}O_x$ Catalyst | | | | | | | | | |
| 8 | 397 | | 78.4 | 6.1 | | 95 | 52.8 | 55.7 | |

TABLE II

FLUID BED (440 CC) PRODUCTION OF MALEIC ANHYDRIDE FROM n-BUTANE USING $V_{1.0}P_{1.2}Co_{0.2}O_x$ CATALYST

| Example No. | Temperature °C. Bath | Temperature °C. Bed | Ratio Air/ Hydrocarbon | Contact Time (Sec.) | WWH | % Conversion | Maleic Anhydride % Yield | Maleic Anhydride % Selectivity | Time On Stream (Hrs.) |
|---|---|---|---|---|---|---|---|---|---|
| 9 | 371 | 380 | 61.9 | 5.84 | 0.015 | 91.6 | 59.5 | 65.0 | 24 |
| 10 | 377 | 385 | 64.6 | 5.20 | 0.016 | 81.3 | 56.5 | 69.5 | 134 |
| 11 | 376 | 383 | 64.6 | 5.20 | 0.016 | 74.8 | 50.6 | 67.6 | 240 |
| 12 | 378 | 386 | 59.9 | 6.08 | 0.014 | 75.8 | 52.8 | 69.6 | 328 |
| 13 | 394 | 398 | 59.8 | 5.86 | 0.015 | 80.6 | 55.8 | 69.3 | 435 |
| 14 | 411 | 422 | 40.4 | 6.15 | 0.019 | 92.4 | 59.2 | 64.1 | 647 |
| 15 | 409 | 420 | 39.3 | 7.04 | 0.017 | 87.0 | 57.0 | 65.5 | 834 |
| 16 | 410 | 422 | 39.6 | 6.95 | 0.018 | 90.6 | 56.4 | 62.3 | 1,026 |
| 17 | 416 | 428 | 26.6 | 8.53 | 0.021 | 76.3 | 49.0 | 68.8 | 1,290 |
| 18 | 400 | 409 | 61.5 | 5.31 | 0.016 | 85.2 | 54.6 | 64.1 | 1,481 |
| 19 | 409 | 422 | 35.5 | 5.19 | 0.027 | 74.9 | 70.4 | 52.8 | 1,630 |
| 20 | 431 | 443 | 39.0 | 6.79 | 0.018 | 93.2 | 57.0 | 61.2 | 1,847 |

TABLE III

FLUID BED (440 CC) PRODUCTION OF MALEIC ANHYDRIDE FROM n-BUTANE USING $V_{1.0}P_{1.2}O_x$ CATALYSTS

| Example No. | Temperature °C. Bath | Temperature °C. Bed | Ratio Air/ Hydrocarbon | Contact Time (Sec.) | WWH | % Conversion | Maleic Anhydride % Yield | Maleic Anhydride % Selectivity | Time On Stream (Hrs.) |
|---|---|---|---|---|---|---|---|---|---|
| $V_{1.0}P_{1.2}O_x$ Catalyst | | | | | | | | | |
| 21 | 386 | 394 | 29.0 | 6.7 | 0.020 | 97.9 | 60.0 | 61.2 | 78 |
| 22 | 394 | 405 | 29.5 | 6.8 | 0.020 | 83.3 | 55.8 | 67.0 | 145 |
| 23 | 403 | 411 | 36.4 | 9.1 | 0.020 | 82.2 | 57.6 | 70.0 | 196 |
| 24 | 426 | 440 | 26.4 | 8.6 | 0.028 | 89.8 | 56.4 | 62.8 | 246 |
| 25 | 425 | 439 | 29.8 | 8.8 | 0.024 | 91.0 | 55.9 | 61.4 | 334 |
| 26 | 425 | 440 | 28.9 | 8.9 | 0.024 | 93.3 | 57.1 | 61.2 | 429 |
| 27 | 425 | 442 | 22.4 | 10.8 | 0.026 | 92.4 | 53.6 | 58.0 | 479 |
| 80% $V_{1.0}P_{1.2}O_x$/20% $SiO_2$ | | | | | | | | | |
| 28 | 376 | 380 | 61.7 | 6.0 | 0.014 | 88.0 | 41.5 | 47.1 | 43 |
| 29 | 405 | 414 | 27.6 | 5.7 | 0.031 | 78.3 | 46.8 | 59.8 | 257 |
| 30 | 431 | 439 | 27.4 | 5.6 | 0.030 | 76.2 | 46.8 | 61.4 | 527 |
| 31 | 438 | 446 | 28.4 | 8.5 | 0.019 | 94.4 | 50.7 | 53.7 | 720 |
| 32 | 438 | 446 | 28.8 | 8.2 | 0.019 | 93.1 | 51.0 | 54.7 | 882 |
| 33 | 438 | 446 | 28.1 | 8.5 | 0.019 | 91.5 | 51.9 | 56.7 | 957 |
| 34* | 438 | 449 | 28.5 | 10.9 | 0.024 | 94.6 | 50.9 | 53.8 | 1,074 |
| 35* | 438 | 449 | 31.2 | 11.1 | 0.023 | 95.6 | 46.0 | 48.2 | 1,285 |
| 36* | 438 | 451 | 27.0 | 8.9 | 0.031 | 86.4 | 48.1 | 55.7 | 1,375 |
| 37* | 439 | 451 | 24.0 | 10.0 | 0.031 | 86.3 | 46.2 | 53.6 | 1,400 |
| 70% $V_{1.0}P_{1.2}O_x$/30% $SiO_2$ | | | | | | | | | |
| 38 | 358 | 367 | 58 | 7.0 | 0.014 | 90.5 | 51.9 | 57.4 | 114 |
| 39 | 359 | 369 | 58 | 7.0 | 0.014 | 91.4 | 52.3 | 57.2 | 138 |
| 40 | 360 | 368 | 58 | 7.0 | 0.014 | 90.9 | 53.7 | 59.1 | 210 |
| 41 | 360 | 375 | 29.7 | 9.1 | 0.021 | 78.6 | 46.3 | 58.9 | 329 |
| 42 | 371 | 384 | 28.8 | 9.8 | 0.019 | 78.4 | 45.5 | 58.1 | 659 |
| 43 | 370 | 382 | 26.8 | 9.8 | 0.020 | 76.2 | 48.9 | 64.2 | 775 |

TABLE III-continued
FLUID BED (440 CC) PRODUCTION OF MALEIC ANHYDRIDE FROM n-BUTANE USING $V_{1.0}P_{1.2}O_x$ CATALYSTS

| Example No. | Temperature °C. Bath | Temperature °C. Bed | Ratio Air/ Hydrocarbon | Contact Time (Sec.) | WWH | % Conversion | Maleic Anhydride % Yield | Maleic Anhydride % Selectivity | Time On Stream (Hrs.) |
|---|---|---|---|---|---|---|---|---|---|
| 44 | 382 | 394 | 27.8 | 9.6 | 0.020 | 77.2 | 45.0 | 58.3 | 965 |
| 45 | 380 | 393 | 28.7 | 9.8 | 0.019 | 76.8 | 44.4 | 57.8 | 1,085 |
| 46 | 380 | 392 | 27.3 | 8.7 | 0.021 | 72.6 | 44.0 | 60.6 | 1,443 |
| 47 | 380 | 388 | 37.6 | 9.4 | 0.014 | 77.6 | 46.7 | 60.1 | 1,826 |

*Reactor outlet pressure 10 PSIG

We claim:

1. A process for the production of maleic anhydride by the oxidation of n-butane with molecular oxygen or an oxygen-containing gas in a fluid bed reactor at a reaction temperature of about 250° C. to 600° C. in the presence of a microspheroidal, fluidizable catalyst containing the mixed oxides of vanadium and phosphorus, wherein said catalysts is prepared by:
   (a) preparing a vanadium phosphorus mixed oxide containing catalyst precursor in an organic liquid;
   (b) comminuting the catalyst precursor to a particle size of less than about one micron average diameter;
   (c) introducing the catalyst precursor into water prior or subsequent to said comminuting to form an aqueous slurry; and
   (d) spray drying said slurry to form microspheroidal catalyst particles.

2. A process as in claim 1, comprising the additional step of calcining the microspheroidal catalyst particles.

3. A process as in claim 1, wherein said catalyst precursor is prepared in an organic liquid slurry.

4. A process as in claim 1, wherein the catalyst precursor is substantially dried prior to introducing the catalyst precursor into water.

5. A process as in claim 1, wherein a substantial portion of said catalyst precursor is comminuted to a particle size of less than about one half micron average diameter.

6. A process as in claim 1, wherein said aqueous slurry has a solids content of about 25 to about 60 weight percent.

7. A process as in claim 1, wherein a substantial portion of said microspheroidal particles have a particle size of less than 300 microns.

8. A process as in claim 1, wherein a substantial portion of said microspheroidal particles have an average diameter of about 20 microns to about 240 microns.

9. A process as in claim 1, wherein said catalyst precursor additionally comprises promoter elements selected from the group consisting of U, Co, Mo, Fe, Zn, Hf, Zr and mixtures thereof.

10. A process as in claim 1, wherein said oxidation occurs at a reactor pressure greater than one atmosphere.

11. A process as in claim 1, wherein said reaction temperature is about 325° C. to 500° C.

12. A process as in claim 1 wherein said catalyst precursor is introduced into water prior to calcining the catalyst precursor.

* * * * *